United States Patent
Kim

(10) Patent No.: US 11,045,130 B2
(45) Date of Patent: Jun. 29, 2021

(54) APPARATUS FOR MONITORING BIOSIGNALS OF FISH WHILE RESUSCITATING THE FISH AT THE SAME TIME, AND METHOD FOR OPERATING THEREOF

(71) Applicant: DAEGU GYEONGBUK INSTITUTE OF SCIENCE & TECHNOLOGY, Daegu (KR)

(72) Inventor: So Hee Kim, Daegu (KR)

(73) Assignee: DAEGU GYEONGBUK INSTITUTE OF SCIENCE & TECHNOLOGY, Daegu (KR)

( * ) Notice: Subject to any disclaimer, the term of this patent is extended or adjusted under 35 U.S.C. 154(b) by 304 days.

(21) Appl. No.: 15/978,826

(22) Filed: May 14, 2018

(65) Prior Publication Data
US 2018/0325405 A1    Nov. 15, 2018

(30) Foreign Application Priority Data

May 12, 2017   (KR) .......................... 10-2017-0059626
Jul. 31, 2017   (KR) .......................... 10-2017-0097029

(51) Int. Cl.
*A61B 5/291*      (2021.01)
*A61D 7/00*       (2006.01)
(Continued)

(52) U.S. Cl.
CPC .............. *A61B 5/291* (2021.01); *A61B 5/688* (2013.01); *A61D 3/00* (2013.01); *A61D 7/00* (2013.01);
(Continued)

(58) Field of Classification Search
CPC .................. A61B 5/0478; A61B 5/688; A61B 2562/0209; A61B 5/6882; A61B 2503/42;
(Continued)

(56) References Cited

U.S. PATENT DOCUMENTS

2009/0131995 A1* 5/2009 Sloan .................... A61N 1/0529
607/3
2017/0164862 A1    6/2017 Dolev et al.
2018/0146923 A1* 5/2018 Fridman .............. A61B 5/0408

FOREIGN PATENT DOCUMENTS

CN           105943033 A    9/2016
WO    WO 2016/009424 A1    1/2016

OTHER PUBLICATIONS

Johnston, L., Ball, R.E., Acuff, S., Gaudet, J., Sornborger, A., Lauderdale, J.D. Electrophysiological Recording in the Brain of Intact Adult Zebrafish. J. Vis. Exp. (81), e51065, doi:10.3791/51065 (2013) (Year: 2013).*

* cited by examiner

*Primary Examiner* — Devin B Henson
*Assistant Examiner* — Joseph A Tombers
(74) *Attorney, Agent, or Firm* — Lex IP Meister, PLLC

(57) ABSTRACT

The present disclosure relates to measuring biosignals (particularly, electroencephalogram) of fish in a non-invasive and multi-channels manner, with a multi-channel electrode array of one or more conductive plates non-invasively attached to the epidermis of the fish outside of the water a; a reference electrode non-invasively attached to the epidermis of the fish outside of the surface of the water; a supply device that supplies a predetermined material and oxygen to the fish outside of the water; and a minute tube inserted into the oral cavity of the fish outside of the water to resuscitate the fish in a stable state to generate normal electroencephalogram.

10 Claims, 2 Drawing Sheets

(51) Int. Cl.
*A61D 7/04* (2006.01)
*A61D 3/00* (2006.01)
*A61B 5/00* (2006.01)

(52) U.S. Cl.
CPC .............. *A61D 7/04* (2013.01); *A61B 5/6882* (2013.01); *A61B 2503/40* (2013.01); *A61B 2503/42* (2013.01); *A61B 2562/0209* (2013.01)

(58) Field of Classification Search
CPC ........ A61B 2503/40; A61D 7/00; A61D 7/04; A61D 3/00
See application file for complete search history.

APPARATUS FOR MONITORING BIOSIGNALS OF FISH WHILE RESUSCITATING THE FISH AT THE SAME TIME, AND METHOD FOR OPERATING THEREOF

CROSS-REFERENCE TO RELATED APPLICATION

This application claims priority to and the benefit of Korean Patent Application No. 10-2017-0059626, filed on May 12, 2017, and Korean Patent Application No. 10-2017-0097029, filed on Jul. 31, 2017, the disclosure of which is incorporated herein by reference in its entirety.

BACKGROUND OF THE INVENTION

Field of the Invention

The present invention relates to a technology of measuring biosignals (particularly, electroencephalogram) of fish in the non-invasive and multiple channels manner, and more specifically, to a technology of measuring biosignals in the non-invasive manner by attaching multi-channels electrodes to the epidermis of fish, while resuscitating the fish outside of the surface of the water at the same time by inserting a minute tube into the oral cavity of the fish.

Description of the Related Art

In general, the basic principle of all experiments carried out in the medical and cosmetic fields is measuring biosignals of animals. This is because, only when biosignals are measured, it can be quantitatively and objectively figured out whether there are significant effects in the experiments.

There are several kinds of biosignals. Among these biosignals, electroencephalogram (EEG) is the field on which human has not been readily studied up to the present, and recently, various studies on this field are in progress.

In the past, in order to study electroencephalogram, only the invasive method was possible. This is because meaningful signals could be obtained only by making an incision or penetration since the brain of animal is a very weak organ and is protected by hard skull.

This invasive method has two problems. One of the problems is that abnormal electroencephalogram may be generated due to external injuries in the invasive process. This is because the brain has a function of controlling body activities so the brain cannot help reacting against external invasion differently from normal. The other one of the problems is that electroencephalogram can be measured only with a single channel. This is because the brain site should be cut only with a size equal to or less than a predetermined size, and for this reason, the number of electrodes inserted into the brain is limited. Thus, there has been a need to find new methods other than the invasive electroencephalogram measuring method.

The method which is attempted recently in consideration of these problems is a technology for measuring electroencephalogram in the non-invasive manner. This technology does not have to apply invasion to the epidermis, which makes it possible to conduct studies through much more channels. Multiple channels have an advantage of improving provision of limited information as compared to the single channel.

The technology for measuring electroencephalogram in the non-invasive manner is a known technology as disclosed in WO2016/009424 A1 (Title of Invention: ELECTRODE HEADSET GRID AND USE THEREOF IN THE NON-INVASIVE BRAIN STIMULATION AND MONITORING; hereinafter, referred as Prior Art Technology 1). The gist of the known technology is provided as below.

Prior Art Technology 1, which relates to a headset in a checkerboard pattern consisting of several non-invasive conductive plates, discloses that this invention allows it to apply electrical stimulation to the brain or measure electroencephalogram (EEG). In the case of Prior Art Technology 1, the non-invasive conductive plate is the main component of the invention, and the invention is characterized by comprising a plurality of the non-invasive conductive plates such that the conductive plates are arranged in a row, wherein several conductive plates form the respective channels, thereby making it possible to measure electroencephalogram through the multiple channels.

Furthermore, since Prior Art Technology 1 does not limit the experimental subject of the apparatus, the Prior Art Technology 1 seems to include animals as well. In this context, CN 105943033 A A1 (Title of Invention: A wearable experimental animal electroencephalogram collection device; hereinafter, referred as Prior Art Technology 2) describes an invention for measuring electroencephalogram of animal in the non-invasive manner. Prior Art Technology 2 is a technology relating to an electroencephalogram collection device which an experimental animal can wear. In particular, it is disclosed that the electroencephalogram collection device of Prior Art Technology 2 is configured to measure electroencephalogram only in the manner of touching the skin, beyond the conventional manner of making an invasion or penetration into an experimental animal in order to measure electroencephalogram.

However, it is impossible to apply the conventional technologies to all experimental subjects without any limitation. In particular, in the case of some species of fish, they are frequently used in experiments since their gene information is similar to the gene information of human. However, there is a great problem in supplying oxygen to the fish when the fish is outside of the water, and in the water, water surrounds around the epidermis and can disturb the electroencephalogram which is measured in the form of fine electric potentials. For these reasons, there is a limitation in applying the conventional technologies without any additional measures.

As mentioned in the conventional technologies, in order to resolve the problem that it is hard to apply the conventional non-invasive electroencephalogram measuring technology to fish, a technology for using a respirator and an electroencephalogram measuring apparatus at the same time in the fish has been required.

CITATION LIST

Patent Literature 1: WO 2016/009424 A1

SUMMARY OF THE INVENTION

The object of the present invention for solving the aforementioned problems is to apply the non-invasive, multi-channels biosignal measuring technology to fish that is positioned outside of the water. In addition, to this end, the further object is to measure biosignals and resuscitate the fish that is position outside of the water for a long period at the same time.

The technical tasks to be achieved by the present invention are not limited to the technical tasks aforementioned, and other technical tasks not mentioned above could be clearly understood to a person having an ordinary skill in the technical field to which the present invention pertains.

The configuration of the present invention for achieving the aforementioned objects is characterized by comprising a multi-channels electrode array that comprises one or more conductive plates on which electricity flows and is non-invasively attached to the epidermis of the brain portion of fish outside of the water and measures different fine potentials generated from the respective portions of the brain; a reference electrode that comprises a conductive plate on which electricity flows and is non-invasively attached to the epidermis of the body of the fish outside of the water and measures the potential which is a reference of the electroencephalogram analysis of the fish; a multi-channels electrode array which receives the potential measured from the multi-channels electrodes; a reference electrode which receives the potential measured from the reference electrode; a supply device which supplies a predetermined material and oxygen to the fish outside of the water; and a minute tube which is connected to the supply device and is inserted into the oral cavity of the fish outside of the water, wherein the supply device and the minute tube supply the predetermined material and oxygen to the fish that is positioned outside of the water, so as to resuscitate the fish in a stable state to generate normal electroencephalogram.

In the embodiment of the present invention, it is characterized in that the multi-channels electrode array comprises two or more conductive plates, wherein the conductive plates of the multi-channels electrodes are respectively attached to the upper epidermis of a certain site, which is necessary for electroencephalogram analysis, among the sites corresponding to the detailed composition of the brain, and measure different fine potentials generated at some sites which are necessary for the corresponding electroencephalogram analysis.

In the embodiment of the present invention, it is characterized by further comprising a signal acquisition and analysis system, wherein the signal acquisition and analysis system receives a potential received from the multi-channels electrodes and potentials received from the reference electrode to generate one electroencephalogram signal through the difference value of the respective potentials.

In the embodiment of the present invention, it is characterized in that the minute tube is grounded to have a ground potential.

In the embodiment of the present invention, it is characterized by further comprising a fixing member that fixes the body of the fish.

In the embodiment of the present invention, it is characterized in that the predetermined material supplied from the supply device is eugenol diluted with water at a proper concentration.

In the embodiment of the present invention, it is characterized in that the multi-channels electrodes and the reference electrode are attached to the epidermis of the fish by the viscosity of mucus on the epidermis of the fish.

In the embodiment of the present invention, it is characterized in that the multi-channels electrodes and the reference electrode are attached to the epidermis of the fish using an adhesive material.

In the embodiment of the present invention, it is characterized in that the multi-channels electrodes and the reference electrode comprise an attachment part to be attached to the epidermis of the fish, wherein the attachment part is made in the form of fine projection or hook.

In the embodiment of the present invention, it is characterized in that the supply device comprises a controller, wherein a predetermined control signal is generated at the controller according to the aspect of one electroencephalogram signal delivered from the signal acquisition and analysis system such that the amounts of the predetermined material and oxygen supplied to the fish from the supply device and the supply time are controlled.

The configuration of the present invention for achieving the aforementioned objects is characterized by a) a step of fixing the fish such that the brain portion faces up on an experiment stand outside of the water; b) a step of inserting a minute tube into the fish to connect the fish to a supply device; c) a step of introducing the predetermined material and oxygen by means of the supply device to resuscitate the fish stably; d) a step of non-invasively attaching a multi-channels electrode array and a reference electrode to the epidermis of the fish to measure the electroencephalogram of the fish; e) a step of measuring potentials from the multi-channels electrodes and the reference electrode during the predetermined time; and f) a step of comparing the potentials measured from the multi-channels electrodes and the reference electrode and collecting and presenting the electroencephalogram generated at the brain.

In the embodiment of the present invention, it is characterized in that the multi-channels electrode array comprises two or more conductive plates, wherein the conductive plates of the multi-channels electrodes are respectively attached to the upper epidermis of a certain site, which is necessary for electroencephalogram analysis, among the sites corresponding to the detailed constitution of the brain, and measures different fine potentials occurring at some sites which are necessary for corresponding electroencephalogram analysis.

In the embodiment of the present invention, it is characterized in that the minute tube is grounded to have a ground potential.

In the embodiment of the present invention, it is characterized that the predetermined material supplied from the supply device is eugenol diluted with water at a proper concentration.

Meanwhile, the embodiments have been explained focusing on those wherein the biosignal measurement is associated with the measurement of electroencephalogram generated at the brain. However, these are just one embodiment of the present invention, and the present invention is not limited to the electroencephalogram measurement aforementioned, and includes those being capable of measuring various forms of electronic biosignals, such as electromyogram and electrocardiogram.

DETAILED DESCRIPTION OF THE PREFERRED EMBODIMENTS

Figure 1:
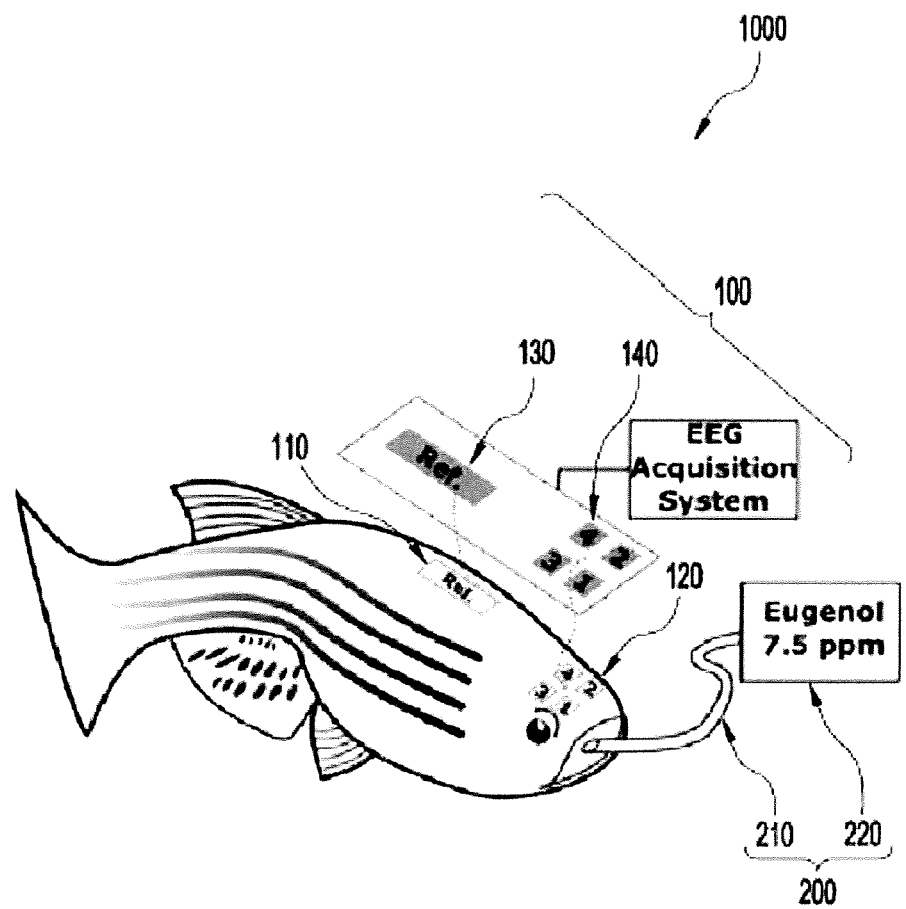
FIG. 1 is a mimetic diagram of the present invention according to one embodiment of the present invention.

Hereinafter, the present invention will be explained with reference to the attached drawings. However, the present invention can be implemented in several different forms, and thus is not limited to the embodiments explained herein.

Further, in the drawings, the portions which are not relevant to the description are omitted to clearly explain the present invention, and in the entire specification, the similar reference numerals are used for the similar portions.

In the entire specification, when it is described that a certain portion is "connected" with other portion, this includes both the case of "being directly connected" and the case of "being indirectly connected" interposing other member therebetween. In addition, when it is described that a certain portion "comprises" a certain component, unless specified otherwise, this means that other components can be further comprised and not be excluded.

The terms used in the present specification are used only for describing the specific embodiments, and are not intended to limit the present invention. A singular expression includes a plurality expression, unless specified otherwise in the context. In the present specification, it should be noted that the terms "comprise" or "have" are used to mean that the features, numbers, steps, operations, components, parts or a combination thereof described in the specification are present, not to exclude the possibility of the presence or addition of one or more other features, numbers, steps, operations, components, parts or a combination thereof.

Hereinafter, the embodiments of the present invention will be explained in more detail with reference to the drawings attached herewith.

As explained in Background of the Invention above, measuring biosignals using animals is the very basic process in the medical and cosmetic fields. In the case of measuring biosignals using animals, as the biosignals of the subject animal are more similar to biosignals of human, better experimental results can be obtained.

In particular, in the case of measuring electroencephalogram among the biosignals using the fish, the experimental process is economic and more efficient as compared to the case of carrying out the experiment using other animals such as mice. This is because that the growth speed of the fish is very fast, the process is economic, and the brain of the fish is considerably genetically similar to the brain of the human. For example, in the case of zebrafish, the expression gene of its brain exhibits about 80% synchronization to the expression gene of the human brain, so the possibility of using the fish for experiments on measuring electroencephalogram is very high.

However, in the case of the fish, despite that the possibility that the fish can be used as an experimental subject is very high, there have been many limitations. First, considering the characteristic of the fish, it is difficult to maintain the respiration outside of the water. Moreover, in the case of measuring electroencephalogram using the invasive method, the measurement for a long time was impossible due to bleeding, etc.

As illustrated in FIG. 1, the present invention comprises two parts: a multi-channels electroencephalogram measuring device 100 and a respirator 200. There is basically no signal exchange between the two parts; however, for more precise experiment, a signal exchange is performed between the two parts and the respective parts may be controlled as predetermined. Hereinafter, the detailed feature of each of the parts will be explained.

First, the electroencephalogram measuring device 100 comprises electrodes. A conductive plate placed on the electrodes is a portion where directly contacts with the epidermis of the fish. Herein, the conductive plates attached to the epidermis of the experimental subject are non-invasive and have multiple channels.

The reason why the conductive plates attached to the epidermis of the experimental subject are non-invasive and have multiple channels is as below. In the past, in order to study electroencephalogram, only the invasive method was possible. This is because meaningful signals could be obtained only by making an incision or penetration since the brain of animal is a very weak organ and is protected by hard skull.

The invasive method had two problems. One of the problems is that an abnormal electroencephalogram may be generated due to external injuries in the invasive process. This is because the brain organ has a function of controlling body activities so the brain cannot help reacting against external invasion differently from normal. The other one of the problems is that electroencephalograms can be measured only with a single channel. This is because the brain site should be cut only with a size equal to or less than a predetermined size, and for this reason, the number of electrodes inserted into the brain is limited.

If the electroencephalogram is measured in the non-invasive method, these problems can be solved. The non-invasive method does not have to apply invasion to the epidermis, which makes it possible to measure through much more channels, and in this case, there are the following advantages as compared to the case of using a single channel.

The concept of electroencephalogram measured through the experiments is the electric potential generated by cells present in the brain. That is, measuring electroencephalogram means the same as measuring potentials. Herein, in order that an experimental subject convulses, there should be superposition and diffusion of abnormally exaggerated action potential.

However, if potentials are measured only with a single electrode (single channel), there is a limitation in measuring the superposition and diffusion phenomenon explained above. Thus, an experiment for measuring potentials for each of the detailed sites of the brain with several electrodes (multiple channels) is required. Hereinafter, it will be described how the present invention measures electroencephalogram non-invasively and using multi-channels.

The electrodes of the electroencephalogram measuring device 100 comprise a reference electrode 110 and multi-channels electrodes 120. The multi-channels electrodes 120 are literally electrodes for measuring electroencephalogram from various sites of the brain through several electrodes. The reference electrode 110 is an electrode for measuring a reference signal of the signals obtained from the multi-channels electrodes 120. That is, the signals received from the multi-channels electrodes 120 are accurately analyzed on the basis of the reference electrode 110. The shape and attachment position of the conductive plates placed on several electrodes aforementioned will be explained below.

Figure 2:
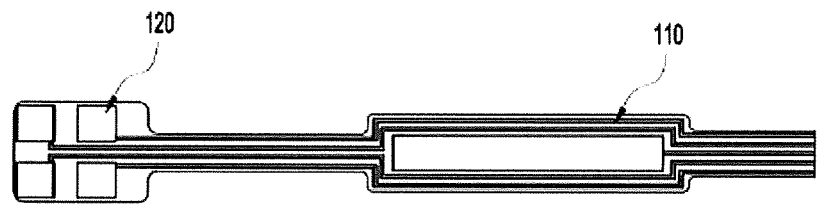
FIG. 2 is a mimetic diagram of the electrode array according to one embodiment of the present invention.

The size of the conductive plates of the present invention may be very small. However, the size may be greater depending on the type of the fish. For example, as illustrated in FIG. 2, in case where zebrafish is an experimental subject, the top and bottom and right and left conductive plates of one multi-channels electrode array 120 may have the sizes not exceeding 1 mm. However, in the case of the reference electrode 110, since it does not have to be attached to the brain site, the size may be greater than the multi-channels electrodes 120. Of course, the size of the reference electrode 110 may vary depending on the length of the body of the experimental subject.

Figure 3:
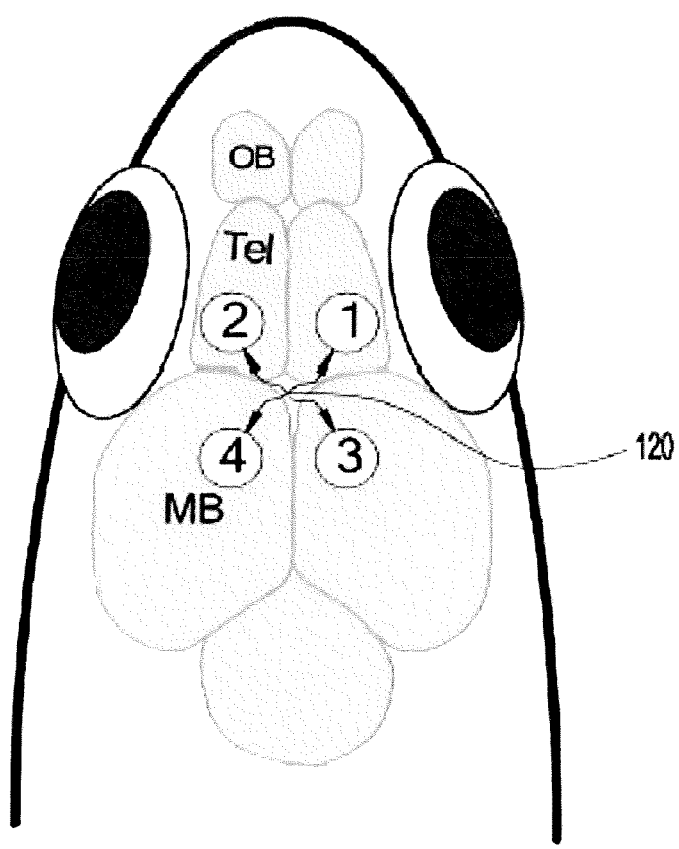
FIG. 3 is a mimetic diagram of the brain structure of the fish according to one embodiment of the present invention.

In the case of the reference electrode 110, the position is distributed depending on the site of the brain. For example, as illustrated in FIG. 3, in the case of zebrafish, the respective portions of the brain are clearly classified in the brain structure. In particular, in the case where the conductive plates are attached to the left and right brain of TEL (telencephalon) portion and the left and right brain of MB (midbrain) portion, electroencephalogram was smoothly measured.

The above conductive plates can use various attachment means while maintaining the various non-invasive method.

As one embodiment, there is a method of temporarily attaching the conductive plates by simply applying pressure to the conductive plates using the viscosity of the epidermis of the fish.

As another embodiment, there is a method of attaching the conductive plates to the epidermis using the viscosity of the epidermis of the fish, and additionally using non-conductive adhesive materials on the non-conducting surface of the electrode array.

As another embodiment, there is a method of attaching the conductive plates to the epidermis using conductive, semiconductive adhesive materials. Here, the output of electroencephalogram measured may be changed depending on how much the adhesive materials are applied onto the conductive plates.

As other embodiment, there is a method of attaching the conductive plates by attaching a fine projection or a hook-shaped attachment part onto the conductive plates.

The electroencephalogram measuring device 100 also comprises a reference electrode 130, a multi-channels electrode 140, and a signal acquisition and analysis system. The reference electrode 130 is located to the reference electrode attachment position 110 to receive electroencephalogram; the multi-channels electrode 140 is located to the multi-channels electrode attachment position 120 to receive electroencephalogram; and the signal acquisition and analysis system collects and analyzes electroencephalogram received from the reference electrode 130 and the multi-channels electrode 140 and then presents the final electroencephalogram.

The respirator 200 part comprises a minute tube 210 and a supply device 220 as components. It is operated in such a manner that filtered oxygen is supplied from the supply device 220 to the oral cavity of the fish through the minute tube 210. The effect of the case of using the respirator in the process of applying the non-invasive electroencephalogram measuring technology to the fish is described as below.

The non-invasive electroencephalogram measuring technology is a technology for measuring signals using multi-channels electrodes attached to the epidermis. Thus, if water is present in the epidermis as in the water, it is hard to non-invasively attach the electrodes themselves.

Furthermore, if water surrounds the epidermis and the conductive plates to attach electrodes as in the water, it is difficult to measure electroencephalogram signals. This is because electroencephalogram signals are generated at the brain in the form of minute potentials, and the surrounding water can disturb the minute potentials. Thus, in order to carry out a non-invasive experiment ideally, the surface of the fish should be in the state where water is removed to some level, like normal terrestrial animals, but not completely dry.

Considering the above facts, it can be figured out that if the non-invasive electroencephalogram measuring technology and the respirator can be used at the same time, many synergistic effects can be obtained.

As mentioned above, in the experimental field using animals, animals that respire through their lungs and animals that respire through their gills are treated differently. That is, since most of technologies focus on the animals that respire through their lungs, in the case of fish that respire through their gills, uniqueness in purpose and remarkability in effect are recognized.

In particular, in the case of the present invention, uniqueness in purpose and remarkability in effect are much more recognized because it is difficult to measure electroencephalogram if an experiment is carried out in the water, and there is a need to carry out the experiment outside of the water. In this context, the prior art technologies just list the general effects, but fail to present the specific field of the fish and present the effect of electroencephalogram detection in such field.

There is a problem when the electroencephalogram measuring technology is to be performed outside of the water. Here, the problem is the respiration of the fish that respire through their gills. In the case of the fish that respire through their gills, a respirator is required since it is difficult to resuscitate the fish outside of the water. If a minute tube 210 is inserted into the oral cavity of the fish as will be explained below, the respiration can be maintained stably.

Here, the reason why the minute tube 210 method is used, not the other respiration method, is because of the respiratory structure of the fish. The fish that respire through their gills filter water through gills to filter oxygen out; herein, when the fish is present outside of of the water, the pre-filtered oxygen should be introduced into the oral cavity deeply.

In addition, for example, in case where the minute tube 210 is grounded, the more detailed electroencephalogram measurement is possible. The electroencephalogram measuring experiment is to measure potentials generated from the brain, and if the minute tube 210 does not have ground potentials, this may influence the potentials measured from the electrodes.

In particular, if a particular material is introduced together with oxygen through the above minute tube 210, much superior effects can be obtained.

Herein, as one example, if a material, i.e. eugenol, is introduced with oxygen, the problem of putting the fish under anesthesia can be solved. Eugenol has been known as a material which has alleviating and anesthetic effects, so this material has been frequently used as a local anesthesia. When a small amount of eugenol diluted with water at a proper concentration, not an undiluted solution, is introduced into the fish, there are advantages that eugenol puts the fish under anesthesia, thereby minimizing the movement during the experiment and minimizing the change of bio-signals due to the movement of the fish, which leads to further improvement of the measurement accuracy.

In addition, if the supply device comprises a controller, much more detailed respirator function can be realized. It can be figured out from the final electroencephalogram presented by the signal acquisition and analysis system how much of the particular material or oxygen should be supplied to the fish, and thereby the controller releases control signals for supplying the particular material or oxygen as much as the value figured out. Based on this control signals, the supply device can supply the set values of the particular material or oxygen, and the experimenter can observe the experimental subject for much longer time in good state.

In consideration of all of the above features, the electroencephalogram measuring process is explained as below.

A step of capturing fish and fixing the fish such that the brain portion faces up on experiment stand outside of the water is the basic preparation process of the experiment. In particular, in the case of the fish that respire through their gills to generally respire in the water, the process for preparing the experiment outside of the water is distinguished from that in the prior art technologies.

Next, there is a step of attaching a respirator to the fish via the minute tube comprised in the respirator and introducing the predetermined material and oxygen via the respirator to resuscitate the fish stably. This is also the preparation process of the experiment, and this is to make the fish stable. This is because accurate electroencephalogram can be measured only when the fish is in the stable state.

Lastly, there is a step of attaching the reference electrode and the multi-channels electrodes for the electroencephalogram measurement, measuring electroencephalogram from the reference electrode and the multi-channels electrodes for a preset time, collecting the measured potentials and presenting the final electroencephalogram. At this step, the difference value between the potentials measured from the reference electrode and the potentials measured from the multi-channels electrodes are expressed with the magnitude of the electroencephalogram.

As explained above, in measuring biosignals according to the present invention, one embodiment of measuring electroencephalogram was explained in detail; however, the present invention is not limited thereto, and the present invention can be utilized for all of the process of measuring various electric biosignals such as electromyogram and electrocardiogram.

The scope of the present invention is defined by the claims that will be explained below, and it should be interpreted that all changes or modifications derived from the meaning and scope of the claims and equivalents thereof are covered by the scope of the present invention.

While the present invention has been described with respect to the specific embodiments, it will be apparent to those skilled in the art that various changes and modifications may be made without departing from the spirit and scope of the invention as defined in the following claims.

The effect of the present invention according to the aforementioned configuration is that the non-invasive biosignal measuring technology which has been recently developed can be applied to the fish.

First, the effect of the non-invasive biosignal measuring technology is compared with the effect of the invasive biosignal measuring technology, as below.

The invasive method had two problems. One of the problems is that an abnormal electroencephalogram may be generated due to external injuries in the invasive process. This is because the brain organ has a function of controlling body activities so the brain cannot help reacting against external invasion differently from normal. The other one of the problems is that electroencephalograms can be measured only with a single channel. This is because the brain site should be cut only with a size equal to or less than a predetermined size, and for this reason, the number of electrodes inserted into the brain is limited.

On the other hand, when biosignals are measured in the non-invasive manner, normal biosignals can be obtained without injuries, and in the aspect of area, a multi-channels electrode can be attached over the larger area without any limitation. Since information of electroencephalogram is very weak, there is a need to measure up to fine signals. Here, if a multi-channels is used, there are advantages as follows when compared to the case of using a single channel.

The electroencephalogram measured through the experiments records potentials generated by cells present in the brain. That is, measuring electroencephalogram means the same as measuring potentials. Herein, in order that an experimental subject convulses, there should be superposition and diffusion of abnormally exaggerated action potentials. However, if potentials are measured only with a single electrode (single channel), there is a limitation in measuring the superposition and diffusion phenomenon explained above. Thus, an experiment for measuring potentials for each of the detailed sites of the brain with several electrodes (multi-channels) is required.

Next, the effect of the case of using the respirator technology in the process of applying the non-invasive biosignal measuring technology to the fish is described as below.

The non-invasive biosignal measuring technology is a technology for measuring signals using a multi-channels electrode attached to the epidermis. Thus, if a large amount of water is present in the epidermis, it is hard not only to attach the electrode itself, but also to measure signals. That is, only when the surface of the fish is dried to some level, like normal terrestrial animals, it is considered to meet the condition where the biosignal detecting technology can be used more smoothly. In this aspect, the synergistic effect of the two technologies would be considerable.

As mentioned above, in the experimental field using animals, animals that respire through their lungs and animals that respire through their gills are treated differently. That is, since most of technologies focus on the animals that respire through their lungs, in the case of fish that respire through their gills, uniqueness in purpose and remarkability in effect are recognized. In particular, in the case of the present invention, uniqueness in purpose and remarkability in effect are much more recognized because it is difficult to measure electroencephalogram if an experiment is carried out in the water, and there is a need to carry out the experiment outside of the surface of the water. In this context, the prior art technologies just list the general effects, but fail to present the specific field of the fish and present the effect of electroencephalogram detection in such field.

There is a problem when the electroencephalogram measuring technology is to be performed outside of the water. Here, the problem is the respiration of the fish that respire through their gills. In the case of the fish that respire through their gills, a respirator is required since it is difficult to resuscitate the fish outside of the water. If a minute tube is inserted into the oral cavity of the fish as will be explained below, the respiration can be maintained stably.

In particular, if a particular material is introduced, in addition to oxygen, through the above respirator, a more superior effect can be generated. In the case of the fish, if the epidermis is too dry, a problem of the respirator would occur.

Herein, as one example, if a material, i.e. eugenol, diluted with water at a proper concentration is used, oxygen can be introduced in the process of diluting eugenol with water. Eugenol has been known as a material which has alleviating and anesthetic effects, so this material has been frequently used as local anesthesia. Thus, by introducing the predetermined concentration of eugenol into the fish, eugenol is used to prevent the unexpected movement of the fish when measuring biosignals of the fish outside of the water and to more improve the accuracy of the measurement of the biosignals.

What is claimed is:

1. An apparatus for non-invasively measuring biosignals of a fish while resuscitating the fish, comprising:
   a multi-channel electrode array having four conductive plates for electricity flow, and configured to be non-invasively attached to an epidermis of the fish when outside of water and to measure different fine potentials generated from respective portions of a brain of the fish;

a reference electrode having a conductive plate for electricity flow and configured to be non-invasively attached to the epidermis of the fish outside of the water to measure a potential which is a reference of an electroencephalogram analysis of the fish and generated from a portion apart from the brain of the fish;

a supply device for supplying a predetermined material and oxygen to the fish outside of the water; and a tube comprising a ground connection for grounding to a ground potential, and configured to be connected to the supply device and configured to be inserted into an oral cavity of the fish outside of the water, wherein the supply device and the tube are configured to supply the predetermined material and oxygen to the fish that is positioned outside of the water, so as to resuscitate the fish in a stable state to generate a normal electroencephalogram, wherein the multi-channel electrode array and the reference electrode are mounted on an elongated sheet which includes an attachment part having a fine projection or hook, or an adhesive material configured to be attached to the epidermis of the fish, wherein the multi-channel electrode array and the reference electrode are located adjacent to respective end portions of the elongated sheet and are located apart from each other, wherein the fish is zebrafish, and wherein the four conductive plates are mounted on the elongated sheet such that the two of the four conductive plates are arranged on the left and right brain of TEL (telencephalon) portion of the zebrafish and the other two of the four conductive plates are arranged on left and right brain of MB (midbrain) portion of the zebrafish.

2. The apparatus for non-invasively measuring biosignals of the fish while resuscitating the fish according to claim 1, wherein the four conductive plates of the multichannel electrode array are configured to be respectively attached to an upper epidermis of a head of the fish and measure different fine potentials generated at sites which are specified for a corresponding biosignal analysis.

3. The apparatus for non-invasively measuring biosignals of the fish while resuscitating the fish according to claim 1, further comprising:

a signal acquisition and analysis system, wherein the signal acquisition and analysis system is configured to receive a potential received from the multi-channel electrode array and the potential received from the reference electrode to generate one biosignal through a difference value of respective potentials.

4. The apparatus for non-invasively measuring biosignals of the fish while resuscitating the fish according to claim 1, further comprising:

a fixing member for fixing a body of the fish.

5. The apparatus for non-invasively measuring biosignals of the fish while resuscitating the fish according to claim 1, wherein the predetermined material to be supplied by the supply device is eugenol diluted with water or other anesthetic drug.

6. The apparatus for non-invasively measuring biosignals of the fish while resuscitating the fish according to claim 1 wherein that the multi-channel electrode array and the reference electrode are configured to be attached to the epidermis of the fish by a viscosity of mucus on the epidermis of the fish.

7. The apparatus for non-invasively measuring biosignals of the fish while resuscitating the fish according to claim 3, wherein the supply device comprises a controller, wherein a predetermined control signal will be generated at the controller according to an aspect of one biosignal delivered from the signal acquisition and analysis system such that amounts of the predetermined material and oxygen supplied to the fish from the supply device and the supply time will be controlled.

8. The apparatus for non-invasively measuring biosignals of the fish while resuscitating the fish according to claim 1, wherein the multi-channel electrode array is configured to be attached to the epidermis of a brain portion of the fish to measure potentials generated from respective portions of the brain, and the biosignal is an electroencephalogram.

9. A method for non-invasively measuring biosignals of a fish, comprising:

a) fixing the fish such that the fish faces up on an experiment stand outside of water;

b) inserting a tube into a fish mouth to connect the fish to a supply device and grounding the tube to a ground potential;

c) introducing a predetermined material and oxygen by the supply device to resuscitate the fish stably;

d) non-invasively attaching multi-channel electrode array and a reference electrode to an epidermis of the fish to measure a biosignal of the fish;

e) measuring potentials from the multi-channel electrodes and the reference electrode during a predetermined time; and f) comparing potentials measured from the multi-channel electrodes and the reference electrode and collecting and presenting the generated biosignals, wherein the multi-channel electrode array has four conductive plates configured to measure different fine potentials generated from respective portions of a brain of the fish, wherein the reference electrode has a conductive plate configured to measure a potential which is a reference of an electroencephalogram analysis of the fish and generated from a portion apart from the brain of the fish, wherein the multi-channel electrode array and the reference electrode are mounted on an elongated sheet which includes an attachment part having a fine projection or hook, or an adhesive material configured to be attached to the epidermis of the fish, wherein the multi-channel electrode array and the reference electrode are located adjacent to respective end portions of the elongated sheet and are located apart from each other, wherein the fish is zebrafish, and wherein the four conductive plates are mounted on the elongated sheet such that the two of the four conductive plates are arranged on the left and right brain of TEL (telencephalon) portion of the zebrafish and the other two of the four conductive plates are arranged on left and right brain of MB (midbrain) portion of the zebrafish.

10. The method for non-invasively measuring biosignals of the fish according to claim 9, wherein the predetermined material supplied by the supply device is eugenol diluted with water or another anesthetic drug.

\* \* \* \* \*